United States Patent [19]

Satoh et al.

[11] Patent Number: 5,194,445
[45] Date of Patent: Mar. 16, 1993

[54] ASCORBIC ACID DERIVATIVE

[75] Inventors: Toshio Satoh; Yasunori Niiro; Hisao Kakegawa; Hitoshi Matsumoto, all of Tokushima, Japan

[73] Assignee: Nippon Hypox Laboratories Incorporated, Tokyo, Japan

[21] Appl. No.: 700,176

[22] PCT Filed: Sep. 11, 1990

[86] PCT No.: PCT/JP90/01157

§ 371 Date: May 20, 1991

§ 102(e) Date: May 20, 1991

[87] PCT Pub. No.: WO90/03471

PCT Pub. Date: Mar. 21, 1991

[30] Foreign Application Priority Data

Sep. 11, 1989 [JP] Japan .................. 1-234871

[51] Int. Cl.$^5$ .................. A61K 43/455; C07D 307/62
[52] U.S. Cl. .................. 514/474; 549/315
[58] Field of Search .................. 549/315; 514/474

[56] References Cited

U.S. PATENT DOCUMENTS 4,780,549 10/1988 Terao et al. .................. 549/315
5,034,543 7/1991 Satoh et al. .................. 549/315
5,061,812 10/1991 Satoh et al. .................. 549/315

Primary Examiner—C. Warren Ivy
Assistant Examiner—Raymond Covington
Attorney, Agent, or Firm—Nixon & Vanderhye

[57] ABSTRACT

The preparation for preventing and curing organ dysfunctions, provided by the present invention, is a medicament having the activity to prevent and cure organ dysfunctions which active oxygen species and active organic radical species would cause, and unconventionally improved in stability in vivo by containing, as an active component, the ascorbic acid derivative of the formula,

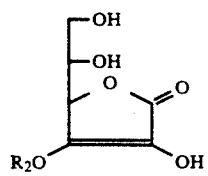

wherein $R_2$ is a group selected from the class consisting of an alkylcarbonyl lower alkyl group of which the terminal alkyl group has 7 inclusive to 15 inclusive carbon atoms, an alkyl group having 9 inclusive to 17 inclusive alkyl groups and an alkoxycarbonyl lower alkyl group of which the terminal alkoxy group has 7 inclusive to 20 inclusive carbon atoms; and the ascorbic acid derivative of the above formula in which $R_2$ is an alkylcarbonyl lower alkyl group of which the terminal alkyl group has 7 inclusive to 15 inclusive carbon atoms is novel and disclosed in the present specification together with the process for its preparation.

7 Claims, No Drawings

ASCORBIC ACID DERIVATIVE

TECHNICAL FIELD

The present invention relates to an ascorbic acid derivative useful as a preparation for preventing and curing an organ dysfunction, particularly as a preparation having a preventive and curing effect on organ dysfunctions caused by active oxygen species and/or active organic radical species which are induced by ischemia, etc.

TECHNICAL BACKGROUND

Recently increasing organ dysfunctions in the heart, brain, kidney, liver, etc., have been found to be caused as follows. An ischemic state (bloodstream malcirculation) causes a failure in supply of an energy source and a metabolic change. Various tissue-disordering factors, which are caused by reperfusion with a bloodstream, destroy or injure cells and tissues of which the resistive strength has been lowered due to the above metabolic change.

In recent years, a study of the above tissue-disordering factors has advanced and showed that active oxygen species or active organic radical species have a large share as a factor for the tissue disorder [I. Fridovich, Archives of Biochemistry and Biophysics, Vol. 247, p. 1 (1968); B. Halliwell, Biochemical Journal, Vol. 219, p. 1 (1984); J. M. McCord, Advance in Free Radical Biology and Medicine, Vo. 2, p. 325 (1986)].

Development of these active oxygen species or active organic radical species during the ischemia-reperfusion and a decrease in endogenous resistive factors are considered to have an essential effect on organ dysfunctions.

SOD (superoxide dismutase) and compounds such as α-tocopherol, ascorbic acid, etc., are considered to eliminate these active oxygen species or active organic radical species, and studies of a therapy using these enzyme and compounds are now under way.

However, SOD shows a short half-life in vivo. Being an enzyme, SOD poses an antigenicity problem having regard to an acquisition method and source. And, α-tocopherol has a defect in that its activity in vivo is low. Ascorbic acid has a defect in that it is easily decomposed and inferior in stability.

JP-A-61-263969 discloses that 2-O-substituted ascorbic ascorbic acid is able to eliminate the above active species and useful as a preparation for preventing and curing the dysfunction of a circulatory system which is one of organ dysfunctions. However, this 2-O-substituted ascorbic acid also has a defect in that it is easily decomposed and poor in stability.

Therefore, the first object of the present invention is to provide a novel ascorbic acid derivative which has the activity to prevent and cure organic dysfunctions caused by active oxygen species and/or active organic radical species induced by ischemia, etc.

The second object of the present invention is to provide a process for the preparation of the above novel ascorbic acid derivative.

Further, the third object of the present invention is to provide a preparation for preventing and curing organic dysfunctions, which contains, as an active component, the above novel ascorbic acid derivative and/or other known ascorbic acid derivative.

DISCLOSURE OF THE INVENTION

That is, the ascorbic acid derivative of the present invention is a novel ascorbic acid derivative of the general formula (Ia),

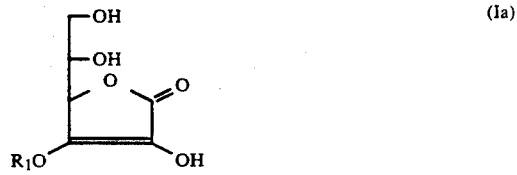

wherein $R_1$ is an alkylcarbonyl lower alkyl group of which the terminal alkyl group has 7 inclusive to 15 inclusive carbon atoms.

The present process for the preparation of an ascorbic acid derivative is a process for the preparation of an ascorbic acid derivative of the general formula (Ia),

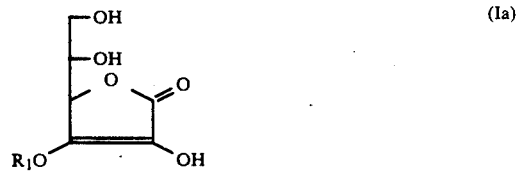

wherein $R_1$ is an alkylcarbonyl lower alkyl group of which the terminal alkyl group has 7 inclusive to 15 inclusive carbon atoms, which comprises treating a compound of the general formula (II),

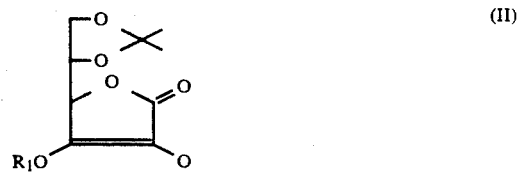

wherein $R_1$ is as defined in the formula (Ia), with an acid thereby to convert the acetal group of said compound to a vic-glycol group.

Further, the present preparation for preventing and curing organ dysfunctions contains, as an active component, an ascorbic acid derivative of the general formula (IA),

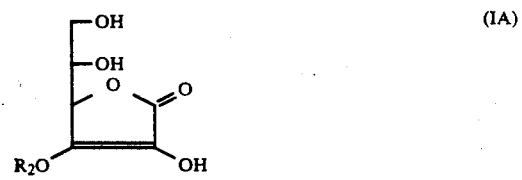

wherein $R_2$ is a group selected from the class consisting of an alkylcarbonyl lower alkyl group of which the terminal alkyl group has 7 inclusive to 15 inclusive carbon atoms, an alkyl group having 9 inclusive to 17 inclusive carbon atoms and an alkoxycarbonyl lower alkyl group of which the terminal alkoxy group has 7 inclusive to 20 inclusive carbon atoms.

In addition, the number of the substituent defined as $R_1$ in the general formula (Ia) for the novel ascorbic acid derivative of the present invention differs from the number of the substituents defined as $R_2$ in the general formula (IA) for the ascorbic acid derivative which is an active component of the preparation of the present invention. $R_1$ is a alkylcarbonyl lower alkyl group, and $R_2$ is selected from three groups including this group (i.e. an alkylcarbonyl lower alkyl group, an alkyl group and an alkoxycarbonyl lower alkyl group). This means that known ascorbic acid derivatives can be also used as an active component in the present preparation for preventing and curing organ dysfunctions.

PREFERRED EMBODIMENTS OF THE INVENTION

To begin with, the novel ascorbic acid derivative of the present invention is explained.

The novel ascorbic acid derivative of the present invention is 3-O-substituted ascorbic acid of the general formula (Ia).

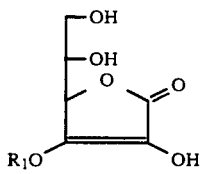

(Ia)

In the above formula, $R_1$ is limited to an alkylcarbonyl lower alkyl group of which the terminal alkyl group has 7 inclusive to 15 inclusive carbon atoms.

The reason for the limitation of the number of carbon atoms of the terminal alkyl group to 7 inclusive to 15 inclusive is that when the number of carbon atoms is not more than 6 or not less than 16, the ability to eliminate active oxygen species or active organic radical species is low and the effect on the prevention and curing of organic dysfunctions is low, which will be made clear in Test Examples to be described later. In the present specification, the term "lower alkyl group" refers to a linear or branched alkyl group having 1 to 4 carbon atoms.

The alkylcarbonyl lower alkyl group as $R_1$ is selected from those of the general formula,

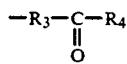

wherein $R_3$ is a lower alkylene group (having 1 to 4 carbon atoms), and optionally may be branched, and $R_4$ is an alkyl group having 7 inclusive to 15 inclusive carbon atoms, and optionally may be branched, and particularly preferred as an alkylcarbonyl lower alkyl group are octylcarbonylmethyl, decylcarbonylmethyl, dodecylcarbonylmethyl, tetradecylcarbonylmethyl, and the like.

Secondly, the present process for the preparation of the novel ascorbic acid derivative of the above general formula (Ia) will be explained below.

In the present process for the preparation of the ascorbic acid derivative, a compound of the general formula (II),

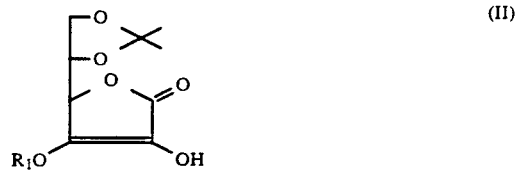

(II)

wherein $R_1$ is the same as $R_1$ defined in the general formula (Ia), is used as a starting material.

The compound of the general formula (II) can be obtained by converting ascorbic acid to an acetal according to a conventional method thereby to obtain 5,6-O-isopropylidene ascorbic acid of the formula (III),

(III)

and then, reacting the above ascorbic acid with an organic halide of the general formula (IV), $$R_1X \qquad (IV)$$

wherein $R_1$ is the same as $R_1$ defined in the general formula (II) and X is a halogen, thereby to etherify a hydroxyl group at 3-position of the compound of the general formula (III).

According to the present process for the preparation of the ascorbic acid derivative, the compound of the general formula (II) obtained above as a starting material is treated with an acid to convert an acetal group of said compound to a vic-glycol group, whereby the intended ascorbic acid derivative (3-O-substituted ascorbic acid) of the general formula (Ia),

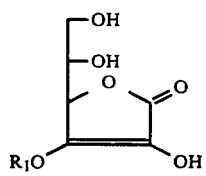

(Ia)

wherein $R_1$ is as defined above, is obtained.

The acid for use in the above reaction can be selected from hydrochloric acid, sulfuric acid, acetic acid, p-toluenesulfonic acid, methanesulfonic acid, etc.

The above reaction is preferably carried out in at least one organic solvent being selected from methanol, ethanol, dioxane, tetrahydrofuran and 1,2-dimethoxyethane and containing a necessary amount of water.

The present preparation for preventing and curing organ dysfunctions will be explained below.

As described above, the preparation for preventing and curing organ dysfunctions, provided by the present invention, contains 3-O-substituted ascorbic acid of the general formula (IA),

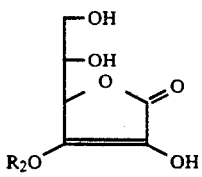

(IA)

and the scope of the group $R_2$ in the formula is broader than that of the group $R_1$ in the general formula (Ia) for the novel ascorbic acid derivative as was already described. Therefore, the ascorbic acid derivative of the general formula (IA) encompasses known compounds.

That is, the group $R_2$ includes the same substituent group as that defined as the group $R_1$ (alkylcarbonyl lower alkyl group of which the terminal alkyl group has 7 inclusive to 15 inclusive carbon atoms), and besides this, it also includes two groups such as an alkyl group having 9 inclusive to 17 inclusive carbon atoms (e.g. decyl, dodecyl, tetradecyl and hexadecyl groups) and an alkoxycarbonyl lower alkyl group of which the terminal alkoxy group has 7 inclusive to 20 inclusive carbon atoms (e.g. decyloxycarbonylmethyl, dodecyloxycarbonylmethyl, tetradecyloxycarbonylmethyl, hexadecyloxycarbonylmethyl and octadecyloxycarbonylmethyl).

The reason for the limitation of the number of carbon atoms of the terminal alkyl group to 7 inclusive to 15 inclusive in the alkylcarbonyl lower alkyl group defined as the group $R_2$ is that when the number of carbon atoms is not more than 6 or not less than 16, the ability to eliminate active oxygen species or active organic radical species is lowered and the effect on the prevention and curing of organ dysfunctions is low.

And, the reason for the limitation of the number of carbon atoms of the alkyl group defined as the group $R_2$ to 9 inclusive to 17 inclusive is that when the number of carbon atoms is not more than 8 or not less than 18, the ability to eliminate active oxygen species and active organic radical species is lowered.

Further, the reason for the limitation of the number of carbon atoms of the terminal alkoxy group to 7 inclusive to 20 inclusive in the alkoxycarbonyl lower alkyl group defined as the group $R_2$ is that when the number of carbon atoms is not more than 6 or not less than 21, the ability to eliminate active oxygen species or active organic radical species is lowered.

The ascorbic acid derivative of the general formula (IA) is excellent in the ability to eliminate active oxygen species or active organic radical species, and is therefore preferably useful as a preparation for preventing injury which these active species cause on a biomembrane and for preventing and curing organ dysfunctions. This ascorbic acid derivative is also advantageous in that it has excellent stability over conventional 2-O-substituted ascorbic acid derivatives.

The form of the preparation for preventing and curing organ dysfunctions is not specially limited, and can be selected from various forms of oral solid preparations such as powders, fine granules, granules, tablets, coated tablets, capsules, etc.; oral liquid preparations such as syrup, etc,; and injection preparation, and the like. And, when the preparation is formed, conventional preparation carriers such as an excipient, a binder a disintegrator, a lubricant, a colorant, a taste and odor modifier, etc., may be incorporated.

The dose of the present preparation for preventing and curing organ dysfunctions differs depending upon disease indications, degrees of symptoms, dosing methods, age and health state of a patient, etc., and therefore, cannot be fixed. In general, however, the ascorbic acid derivative of the general formula (IA) as an active component is dosed at a rate of 0.1 to 500 mg/kg/day, whereby the intended effect can be obtained.

The present invention will be explained by reference to Examples.

PREPARATION EXAMPLE 1

Preparation of novel ascorbic acid derivative (Ia)

(1) Synthesis of 3-O-dodecylcarbonylmethyl-5,6-O-isopropylidene ascorbic acid as a starting material 4.7 Grams of 5,6-O-isopropylidene ascorbic acid was dissolved in 40 ml of DMSO, 1.8 g $NaHCO_3$ was added, and the resultant mixture was stirred.

6.3 Grams of methyl bromide dodecyl ketone was added to the above mixture, and the resultant mixture was heated to 60° C. and stirred for 20 hours for etherification.

Added to the resultant reaction liquid were 500 ml of ethyl acetate and 200 ml of $H_2O$, and the mixture was shaken to separate an organic layer and recover it.

The organic layer was washed with water, dried and concentrated under reduced pressure, and the resultant residue was subjected to silica gel chromatography with benzene and ethyl acetate (benzene:ethyl acetate=1:5) to give 3-O-dodecylcarbonylmethyl-5,6-O-isopropylidene ascorbic acid [a compound of the above formula (II) in which $R_1$ is dodecylcarbonylmethyl] as a starting material. The yield thereof was 6.0 g.

(2) Synthesis of 3-O-dodecylcarbonylmethyl ascorbic acid as an intended substance 5.5 Grams of the 3-O-dodecylcarbonylmethyl-5,6-O-isopropylidene ascorbic acid obtained in (1) was dissolved in 300 ml of a methanol/tetrahydrofuran mixed solution (methanol:tetrahydrofuran=1:2), and 100 ml of 2N-HCl was added. The resultant mixture was stirred at 50° C. for 1 hour.

The reaction liquid was concentrated under reduced pressure, and 500 ml of ethyl acetate was incorporated to the resultant residue.

The resultant organic layer was consecutively washed with $H_2O$, dilute $NaHCO_3$ and $H_2O$, and dried and concentrated under reduced pressure to give 4.9 g of a white powder. The white powder was recrystallized from methylene chloride:n-hexane to give 3-O-dodecylcarbonylmethyl ascorbic acid as an intended substance {a compound of the general formula (Ia) in which $R_1$ is dodecylcarbonylmethyl [this compound is referred to as a compound (Ia3) hereinafter]}. The yield thereof was 10 g.

Melting point: 113°–114° C.

NMR (TMS, MeOHd4): 0.89 (3H, t), 1.29 (20H, m), 2.51 (2H, t), 3.69 (2H, m), 3.93 (H, m), 4.88 (H, d), 5.11 (2H, dd).

PREPARATION EXAMPLES 2-4

Preparation of Other Novel Ascorbic Acid Derivatives (Ia)

According to Preparation Example 1, there were prepared a compound of the general formula (Ia) in which $R_1$ was octylcarbonylmethyl (Ia1), a compound of the general formula (Ia) in which $R_1$ was decylcarbonylmethyl (Ia2), and a compound of the general formula (Ia) in which $R_1$ was tetradecylcarbonylmethyl (Ia4). The melting points of these compounds are summarized in Table 1.

REFERENTIAL PREPARATION EXAMPLE 1

Preparation of Known Ascorbic Acid Derivative Included in Ascorbic Acid Derivative (IA)

(1) Synthesis of 3-O-dodecyl-5,6-O-isopropylidene ascorbic acid 4.3 Grams of 5,6-O-isopropylidene ascorbic acid was dissolved in 30 ml of DMSO, and 1.8 g of finely milled $NaHCO_3$ was added. The resultant mixture was stirred at room temperature for about 0.5 hour, and 5.6 g of dodecyl bromide was added thereto. The mixture was heated to 50° to 60° C. and stirred continuously for 10 to 20 hours. The reaction liquid was cooled with water, and then, 100 ml of $H_2O$ and 100 ml of ethyl acetate were added. The resultant mixture was shaken to separate an organic layer and recover it. A water layer was shaken further twice together with 100 ml of ethyl acetate to separate organic layers and recover them. The combined organic layers were washed with water, dried and concentrated under reduced pressure. The resultant residue was subjected to silica gel chromatography with benzene:ethyl acetate (8:1) to give 4.6 g of 3-O-dodecyl-5,6-O-isopropylidene ascorbic acid.

(2) Synthesis of 3-O-dodecyl ascorbic acid 4.0 Grams of the 3-O-dodecyl-5,6-O-isopropylidene ascorbic acid obtained in (1) was dissolved in a mixed solution consisting of 15 ml of THF and 6 ml of methanol, and 6 ml of 2N-HCl was added. The resultant mixture was stirred at room temperature for 10 to 20 hours (for 2 to 4 hours at 50° to 70° C.). Low-boiling components were removed under reduced pressure, and the reaction mixture was adjusted to pH 3 with a saturated $NaHCO_3$ solution. The reaction mixture was shaken three times with ethyl acetate of which the amount was twice as large as that of the reaction mixture. The organic layers were separated and recovered. The combined organic layers were washed with water, dried and then concentrated under reduced pressure to give a residue. Petroleum ether and methylene chloride were added to the residue, and the mixture was filtered to recover a white precipitate. The white precipitate was recrystallized from methylene chloride-n-hexane to give 3-O-dodecyl ascorbic acid {a compound of the general formula (IA) in which $R_2$ is dodecyl [this compound is referred to as a compound (IA2) hereinafter]}. The yield thereof was 3.2 g.
Melting point: 86°–88° C.

REFERENTIAL PREPARATION EXAMPLE 2

Preparation of Known Ascorbic Acid Derivative Included in Ascorbic Acid Derivative (IA)

According to Referential Preparation Example 1, there were prepared a compound of the general formula (IA) in which $R_2$ was decyl (IA1), a compound of the general formula (IA) in which $R_2$ was tetradecyl (IA3), a compound of the general formula (IA) in which $R_2$ was hexadecyl (IA4), a compound of the general formula (IA) in which $R_2$ was decyloxycarbonylmethyl (IA5) and a compound of the general formula (IA) in which $R_2$ was octadecyloxycarbonylmethyl (IA6). The melting points of these compounds are also summarized in Table 1.

TEST EXAMPLE 1

Activity to Inhibit Hyperoxidation of Lipid of Rat Liver Microsome

A rat liver microsome was prepared according to a conventional method, and suspended in 1.15% KCl to obtain a microsome suspension.

The above microsome suspension in an amount equivalent to 2 mg of a protein was added to a tris-HCl buffer (pH 7.4) to which NADPH, ADP and $FeCl_3$ had been added such that the final concentrations were 0.2 mM of NADPH, 1 mM of ADP and 10 $\mu$M of $FeCl_3$.

A dimethylformamide (DMF) solution of each of test compounds in an amount of 10 $\mu$l or DMF in an amount of 10 $\mu$l was added such that the total amount of each of the mixtures was 1 ml, and then, the mixtures were kept at 37° C. for 20 minutes. In addition, the test compounds were added in such amounts that their final concentrations became $10^{-5}$M.

Thereafter, according to a thiobarbituric acid method, the above mixtures were measured for an amount of peroxide lipid formed. The inhibiting activities of the test compounds were compared with that of the group containing the solvent (DMF) alone, and the results were expressed as an inhibition ratio (%). Table 1 shows the results.

TABLE 1

| Compound name | Preparation process | $R_1$ or $R_2$ | Melting point (°C.) | Lipid hyperoxidation inhibition ratio (%) |
| --- | --- | --- | --- | --- |
| Comparative compound (a) | — | $CH_2CO(CH_2)_5CH_3$ | 99–100 | 27 |
| Compound (Ia1) | Preparation Example 2 | $CH_2CO(CH_2)_7CH_3$ | 109–110 | 64 |
| Compound (Ia2) | Preparation Example 2 | $CH_2CO(CH_2)_9CH_3$ | 105–106 | 88 |
| Compound (Ia3) | Preparation Example 1 | $CH_2CO(CH_2)_{11}CH_3$ | 113–114 | 85 |
| Compound (Ia4) | Preparation Example 2 | $CH_2CO(CH_2)_{13}CH_3$ | 116–117 | 65 |
| Comparative compound (b) | — | $CH_2CO(CH_2)_{15}CH_3$ | 113–116 | 43 |
| Comparative compound (c) | — | $(CH_2)_7CH_3$ | 58–60 | 40 |
| Compound (IA1) | Referential Preparation Example 2 | $(CH_2)_9CH_3$ | 73–75 | 91 |
| Compound (IA2) | Referential Preparation Example 1 | $(CH_2)_{11}CH_3$ | 86–88 | 91 |

TABLE 1-continued

| Compound name | Preparation process | $R_1$ or $R_2$ | Melting point (°C.) | Lipid hyperoxidation inhibition ratio (%) |
|---|---|---|---|---|
| Compound (IA3) | Referential Preparation Example 2 | $(CH_2)_{13}CH_3$ | 68–69 | 81 |
| Compound (IA4) | Referential Preparation Example 2 | $(CH_2)_{15}CH_3$ | 73–74 | 74 |
| Comparative compound (d) | Referential Preparation Example 2 | $(CH_2)_{17}CH_3$ | 102–103 | 45 |
| Compound (IA5) | Referential Preparation Example 2 | $CH_2COO(CH_2)_9CH_3$ | 110–111 | 72 |
| Compound (IA6) | Referential Preparation Example 2 | $CH_2COO(CH_2)_{17}CH_3$ | 92–93 | 73 |

Table 1 shows the following:

(i) The compounds (Ia1), (Ia2), (Ia3) and (Ia4) which were novel ascorbic acid derivatives had a lipid hyperoxidation inhibition ratio of 64 to 88%, i.e. exhibited and excellent effect. In contrast, the comparative compounds (a) and (b) were as poor as 27% and 43% in the inhibition ratio, i.e. inferior in effect.

As is shown in Table 1, in the compounds (Ia1), (Ia2), (Ia3) and (Ia4), the terminal alkyl groups of the alkylcarbonyl lower alkyl groups as $R_1$ has 8 to 14 carbon atoms, whereas the terminal alkyl groups of the alkylcarbonyl lower alkyl groups as $R_1$ in the comparative compounds (a) and (b) had 6 and 16 carbon atoms, respectively. The above remarkable differences in the lipid hyperoxidation inhibition ratio between the compound group of (Ia1), (Ia2), (Ia3) and (Ia4) and the comparative compound group of (a) and (b) clearly show the significance or criticality of the limitation of the number of carbon atoms to 7 inclusive to 15 inclusive in the terminal alkyl group of the alkylcarbonyl lower alkyl group.

(ii) The compounds (IA1), (IA2), (IA3) and (IA4) which were known ascorbic acid derivatives had a lipid hyperoxidation inhibition ratio of 73 to 91%, i.e. exhibited an excellent effect. In contrast, the comparative compounds (c) and (d) were as poor as 40% and 45% in the inhibition ratio, i.e. inferior in effect.

As is shown in Table 1, the alkyl groups as $R_2$ in the compounds (IA1), (IA2), (IA3) and (IA4) had 10 to 16 carbon atoms, whereas the alkyl groups as $R_2$ in the comparative compounds (c) and (d) has 8 and 18 carbon atoms, respectively. The above remarkable differences in the lipid hyperoxidation inhibition ratio between the compound group of (IA1), (IA2), (IA3) and (IA4) and the comparative compound group of (c) and (d) clearly show the significance or criticality of the limitation of the number of carbon atoms of the alkyl group to 9 inclusive to 17 inclusive.

(iii) Similarly, the compound of the general formula (IA) in which $R_2$ is decyloxycarbonylmethyl, i.e. the compound (IA5), and the compound of the general formula (IA) in which $R_2$ is octadecyloxycarbonylmethyl, i.e. the compound (IA6) also had an inhibition ratio of 72 to 73%, i.e. exhibited an excellent effect.

The foregoing results have showed that the compounds according to the present invention have the excellent ability to eliminate active oxygen species or active organic radical species.

Therefore, these compounds produce an excellent effect on inhibition of biomembrane injury which active oxygen species or active organic radical species would cause.

TEST EXAMPLE 2

Activity to Inhibit Ventricular Arrhythmia During Coronary Occlusion-Reperfusion in Rat Heart Five to ten male Wistar rats (weight 230 to 460 g per rat) were used as one group for each of test compounds. Each of the rats was anesthetized with sodium pentobarbital, and electrocardiograms thereof were recorded with standard lead II.

The rats were subjected to thoracotomy under artificial respiration, and left coronary artery ramus anterior descendenses were ligated for 5 minutes and then perfused. And, the frequency of occurrence of ventricular arrhythmia was observed for 10 minutes.

In addition, each of test compounds was suspended in a physiological saline containing 1% olive oil and 1% Tween 80, and the resultant suspensions were administered into femoral veins 2 minutes before the coronary occlusion, or orally administered 1 hour before the coronary occlusion, such that the amounts of said compounds were as predetermined.

Table 2 shows the results.

TABLE 2

| Compound | Administration method*2 | Dose (mg/kg) | Total time of arrhythmia occurrence (second)*3 (mean + S.E.) |
|---|---|---|---|
| Compound (Ia3) | i.v. | 0.3 | 471.0 ± 73.6 (n = 8) |
| | | 1 | 216.1 ± 59.6 (n = 8) |
| | | 3 | 273.5 ± 93.8 (n = 8) |
| | | 10 | 203.8 ± 91.0 (n = 8) |
| | | 30 | 150.5 ± 79.8 (n = 8) |
| Vehicle*1 | i.v. | 0 | 536.3 ± 62.3 (n = 8) |
| Compound (Ia3) | p.o. | 10 | 378.2 ± 61.4 (n = 10) |
| | | 30 | 313.3 ± 81.7 (n = 10) |
| | | 100 | 85.4 ± 28.9 (n = 10) |
| | | 300 | 123.6 ± 43.7 (n = 10) |
| Vehicle*1 | p.o. | 0 | 518.6 ± 41.3 (n = 10) |
| Compound (IA2) | i.v. | 10 | 48.2 ± 19.9 (n = 5) |
| Vehicle*1 | i.v. | 0 | 446.5 ± 96.1 (n = 6) |
| Compound (IA1) | i.v. | 1 | 290.8 ± 87.7 (n = 5) |
| | | 10 | 210.8 ± 81.2 (n = 5) |
| Compound (Ia2) | i.v. | 1 | 205.2 ± 91.0 (n = 6) |
| Vehicle*1 | i.v. | 0 | 564.8 ± 20.8 (n = 5) |

*1: As a vehicle, a physiological saline containing 1% olive oil and 1% Tween 80 was administered.
*2: i.v.—intravenously
p.o.—per os
*3: Total time of arrhythmia occurrence means a total of periods of time during which arrhythmia was observed for the observation time of 10 minutes (600 seconds).

When a left coronary artery ramus anterior descendence is occluded for 5 minutes and then reperfused, ventricular arrhythmia typified by ventricular tachycardia (VT) and ventricular fibrillation (VF) occurs.

As is clearly shown in Table 2, the groups of rats to which the vehicles had been administered repeatedly showed VT and VF like a fit during 10 minutes' observation after the perfusion. Meanwhile, the compound (Ia2) significantly inhibited occurrence of this arrhythmia when 1 mg/kg of it was intravenously administered; the compound (Ia3) showed the same significant inhibition when not less than 1 mg/kg of it was intravenously administered and when not less than 10 mg/kg of it was orally administered; the compound (IA1) showed the same significant inhibition when not less than 1 mg/kg of it was intravenously administered; and the compound (IA2) showed the same significant inhibition when not less than 10 mg/kg of it was intravenously administered.

TEST EXAMPLE 3

Action on Survival Rate of Ischemic Brain Model Mouse

Thirteen to fifty-six ICR male mice were used as one group for each of test compounds. Each of the mice was anesthetized by intraperitoneal administration of sodium pentobarbital, the bilateral carotid arteries were exposed, a thread was put around the arteries, and the skin was sutured with one end of the thread outside the body.

Three days after the suture of the skin, the bilateral carotid arteries were ligated for 3 minutes, and then reperfused to obtain ischemic brain model mice. And, a survival rate in each group 24 hours after the ligation-reperfusion of bilateral carotid arteries was determined.

In addition, each of the test compounds was suspended in a physiological saline containing 1% olive oil and 1% Tween 80, and the suspension was orally administered one hour before the ligation of the bilateral carotid arteries such that the amount of each test compound was 100 mg/kg.

Table 3 shows the results.

TABLE 3

| Compound | Dose by oral administration (mg/kg) | Survival rate (%) (number of mice in one group) |
|---|---|---|
| Compound (Ia3) | 100 | 80.0 (n = 15) |
| Compound (IA1) | 100 | 77.0 (n = 13) |
| Vehicle*1 | 0 | 51.7 (n = 56) |

*1: As a vehicle, a physiological saline containing 1% olive oil and 1% Tween 80 was administered.

As in clearly shown in Table 3, the survival rate of the group of mice to which the compound (IA3) or (IA1) was administered is significantly higher than that of the group of mice to which the vehicle was administered, and the compounds (Ia3) and (IA1) therefore have the activity to prevent and cure the brain dysfunction induced by the ligation-reperfusion of bilateral carotid arteries.

TEST EXAMPLE 4

Action on $CCl_4$ Liver Dysfunction

Fourteen and seventeen ICR male mice were used as one group for each test. Each of the mice was hypodermically administered in its dorsal portion with 10 ml/kg of a solution of 10% $CCl_4$ in olive oil to develop acute hepatitis, and the serum obtained by centrifugation of a blood sample taken from each mouse 48 hours after the administration was measured on GOT (glutamic-oxaloacetic transaminase) activity and GPT (glutamic-pyruvic transaminase) activity with an autoanalyzer (AU550, supplied by Olympus K.K.).

In addition, the test compound was suspended in physiological saline containing 1% olive oil and 1% Tween 80, and the resultant suspension was orally administered three times in total, immediately after the $CCl_4$ administration and in the morning and evening on the day thereafter, such that the dose of each test compound was 100 mg/kg/one time administration.

Table 4 shows the results.

TABLE 4

| Compound | Dose (mg/kg) | Number of mice in one group | GOT activity*2 (mean ± S.E) | GPT activity*2 mean = ± S.E) |
|---|---|---|---|---|
| Compound (Ia3) | 100 | 14 | 445.0 ± 69.0 | 1,406.4 ± 185.2 |
| Vehicle*1 | 0 | 17 | 887.6 ± 266.4 | 2,650.0 ± 387.9 |

*1: As a vehicle, a physiological saline containing 1% olive oil and 1% Tween 80 was administered.
*2: Unit/l As is clearly shown in Table 4, the compound (Ia3) significantly reduced the GOT activity value and GPT activity value when 100 mg/kg of it had been orally administered. In the $CCl_4$ hepatitis, $CCl_4$ corresponds to an active organic radical species. It is therefore shown that the compound (Ia3) has the activity to prevent and cure the liver dysfunction which the active organic radical species would cause.

TEST EXAMPLE 5

Action on Ischemic Acute Renal Insufficiency

Four male Wistar rats (weight: about 200 g per rat) were used as one group for each test. Each of the rats was anesthetized with sodium pentobarbital, the right kidney was extirpated, and immediately thereafter, 100 IU/kg of heparin was intravenously administered to its tail. Eight minutes after the administration, the left renal artery was ligated with a suture, and 60 minutes after the ligation, and the renal artery was reperfused by unligating the suture to develop ischemic acute renal insufficiency in each of the rats.

Immediately before the administration of sodium pentobarbital and 72 hours after the reperfusion, blood samples were taken from the tail artery of each rat, and the serums obtained by centrifugation of the sample bloods were respectively measured for a blood urea nitrogen (BUN) amount and a creatinine amount, indices for renal insufficiency, with an autoanalyzer (AU550, supplied by Olympus K.K.).

In addition, the test compound was suspended in a physiological saline containing 1% olive oil and 1% Tween 80, and the resultant suspension was intravenously administered to the tail of each rat 10 minutes before the administration of sodium pentobarbital or 10 minutes before the reperfusion such that the dose of the test compound was 10 mg/kg or 30 mg/kg.

Table 5 shows the results.

TABLE 5

| Compound | Dose (mg/kg) | Number of rats in one group | BUN amount*3 (mean ± S.E.) | Creatinine amount*3 (mean ± S.E.) |
|---|---|---|---|---|
| Compound (Ia3) | 10 | 4 | 33.8 ± 6.1 | 0.93 ± 0.05 |
|  | 30 | 4 | 34.1 ± 8.9 | 1.04 ± 0.12 |
| Vehicle*1 | 0 | 4 | 60.1 ± 10.2 | 1.53 ± 0.15 |
| Normal values*2 | — | 4 | 14.1 ± 1.5 | 0.53 ± 0.04 |

*1: As a vehicle, a physiological saline containing 1% olive oil and 1% Tween 80 was administered.
*2: Obtained from the group of rats, to which the vehicle had been administered, before the extirpation.
*3: unit mg/dl As is clearly shown in Table 5, 72 hours after the reperfusion, the BUN and creatinine amounts of the groups of rats to which the compound (Ia3) was administered are significantly smaller than those of the group of rats to which the vehicle was administered. This result shows that the compound (Ia3) has the activity to prevent ischemic renal insufficiency.

TEST EXAMPLE 6

Stability Test

A tris-HCl buffer having pH of 9.0 was added to each of alcohol solutions of the compounds (Ia2), (Ia3), (IA2) and 2-O-dodecyl ascorbic acid, which was a position isomer of the compound (IA2), in such a manner that the amount of the buffer was 100 times as large as that of each alcohol solution.

The test compounds in the solutions which were allowed to stand at room temperature were quantitatively determined with time to measure their stability.

As a result, the 2-O-dodecyl ascorbic acid was completely decomposed at room temperature after 9 to 12 hours, whereas the compounds (Ia2), (Ia3), and (IA2) showed residual contents of not less than 69%, not less than 80% and not less than 75% at room temperature after 24 hours.

TEST EXAMPLE 8

Acute Toxicity Test on Mouse

Male 3-ICR mice (10 weeks of age) were used. The compounds (Ia2), (Ia3) and (IA2) were intravenously administered to the mice in such a manner that the doses of each of the compounds were 30 mg/kg and 100 mg/kg. For one week after the administration, symptoms were observed. The group of mice to which 100 mg/kg of the compound (Ia2) has been administered showed a sedate state, and yet recovered within 10 minutes. During the observation for one week, no death was found in any one of the groups of mice.

As explained hereinabove, according to the present invention, there is provided a novel ascorbic acid derivative having the activity to prevent and cure organ dysfunctions which active oxygen species and active organic radical species would cause. Further, according to the present invention, there is provided a process for the preparation of the above novel ascorbic acid derivative. Furthermore, according to the present invention, there is provided a preparation containing, as an active component, the above novel ascorbic acid derivative and/or other known ascorbic acid derivative.

What is claimed is:

1. An ascorbic acid derivative of the formula (Ia)

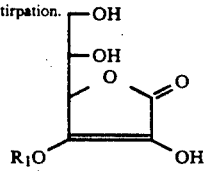

(Ia)

wherein $R_1$ is an alkylcarbonyl lower alkyl group of which the terminal alkyl group has 7 inclusive to 15 inclusive carbon atoms.

2. An ascorbic acid derivative according to claim 1, wherein the alkylcarbonyl lower alkyl group is a member selected from the group consisting of octylcarbonylmethyl, decylcarbonylmethyl, dodecylcarbonylmethyl and tetradecylcarbonylmethyl.

3. A composition for preventing or treating an organic dysfunction, which contains, together with a pharmaceutically acceptable carrier, an effective amount of, as an active component, an ascorbic acid derivative of the formula (IA),

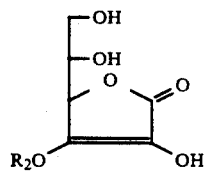

wherein $R_2$ is a group selected from the class consisting of an alkylcarbonyl lower alkyl group of which the terminal alkyl group has 7 inclusive to 15 inclusive carbon atoms, an alkyl group having 9 inclusive to 17 inclusive carbon atoms and an alkoxycarbonyl lower alkyl group of which the terminal alkoxy group has 7 inclusive to 20 inclusive carbon atoms.

4. The composition according to claim 2, wherein the alkylcarbonyl lower alkyl group is a member selected from the group consisting of octylcarbonylmethyl, decylcarbonymethyl, dodecylcarbonylmethyl and tetradecylcarbonylmethyl.

5. The composition according to claim 3, wherein the alkyl group is a member selected from the group consisting of decyl, dodecyl, tetradecyl and hexadecyl.

6. The method according to claim 3, wherein the alkoxycarbonyl lower alkyl group is a member selected from the group consisting of decyloxycarbonylmethyl, dodecyloxycarbonylmethyl, tetradecyloxycarbonylmethyl, hexadecyloxycarbonylmethyl and octadecyloxycarbonylmethyl.

7. A method of preventing or treating a dysfunction of at least one organ selected from heart, brain, kidney and liver, said dysfunction being caused by active oxygen species or active organic radical species, comprising administering to a person in need of same an effective amount of a composition which contains, together with a pharmaceutically acceptable carrier, an effective amount of, as an active component, an ascorbic acid derivative of the formula (IA),

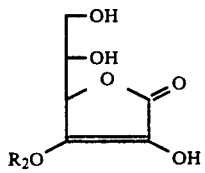

wherein $R_2$ is a group selected from the class consisting of an alkylcarbonyl lower alkyl group of which the terminal alkyl group has 7 inclusive to 15 inclusive carbon atoms, an alkyl group having 9 inclusive to 17 inclusive carbon atoms and an alkoxycarbonyl lower alkyl group of which the terminal alkoxy group has 7 inclusive to 20 inclusive carbon atoms.

* * * * *